United States Patent [19]

Garbe

[11] Patent Number: 5,057,606

[45] Date of Patent: * Oct. 15, 1991

[54] FORM-IN-PLACE POLYSACCHARIDE GELS

[75] Inventor: James E. Garbe, Inver Grove Heights, Minn.

[73] Assignee: Minnesota Mining and Manufacturing Company, St. Paul, Minn.

[*] Notice: The portion of the term of this patent subsequent to Aug. 14, 2007 has been disclaimed.

[21] Appl. No.: 301,164

[22] Filed: Jan. 24, 1989

[51] Int. Cl.$^5$ .................. A61L 15/42; A61L 25/00
[52] U.S. Cl. ........................ 536/54; 424/44; 424/445; 604/85
[58] Field of Search .............. 536/54; 424/44, 445; 604/85

[56] References Cited

U.S. PATENT DOCUMENTS

| | | | |
|---|---|---|---|
| 1,365,183 | 1/1921 | Moffatt | 604/85 |
| 2,441,729 | 5/1948 | Steiner | 426/271 |
| 2,756,874 | 7/1956 | Erickson et al. | 206/221 |
| 2,918,375 | 12/1959 | Gibsen | 426/575 |
| 3,455,701 | 7/1969 | Miller et al. | 426/575 |
| 4,381,947 | 5/1983 | Pellico | 100/38.51 |
| 4,401,456 | 8/1983 | Connick, Jr. | 71/88 |
| 4,432,756 | 2/1984 | Urquhart et al. | 604/85 |
| 4,538,918 | 9/1985 | Mittleman | 604/85 |
| 4,613,497 | 9/1986 | Chavkin | 376/416 |
| 4,834,714 | 5/1989 | Lascar et al. | 604/85 |
| 4,948,575 | 8/1990 | Cole et al. | 424/44 |

FOREIGN PATENT DOCUMENTS 424956 8/1982 Sweden.
1579324 2/1976 United Kingdom.

OTHER PUBLICATIONS

Article Entitled "Improved Method for Preparation of Fruit-Simulating Alginate Gels," Claire Pelaez and Marcus Karel, from the *Journal of Food Processing and Preservation*, vol. 5, pp. 63–81 (1981).

Article Entitled "In Vitro Evaluation of Alginate Gel Systems as Sustained Release Drug Delivery Systems," from the *Journal of Controlled Release*, vol. 3, pp. 167–175 (1986).

Chemical Abstracts, vol. 83; No. 3; Jul. 21, 1975; p. 547; Abstract No. 28563y.

Chemical Abstracts, vol. 103; No. 24; Dec. 16, 1985; p. 325; Abstract No. 200899g.

Chemical Abstracts, vol. 98; No. 24; Jun. 13, 1983; p. 377; Abstract No. 20445q.

Primary Examiner—Ronald W. Griffin
Attorney, Agent, or Firm—Gary L. Griswold; Walter N. Kirn; Gregory A. Evearitt

[57] ABSTRACT

A method and article useful for preparing stable polysaccharide gels from aqueous solutions of water-soluble polysaccharides bearing pendant carboxylate groups. The gels produced may be of the foamed or nonfoamed variety.

26 Claims, No Drawings

FORM-IN-PLACE POLYSACCHARIDE GELS

TECHNICAL FIELD

The present invention relates to the preparation of polysaccharide gels and in particular to a process and article useful for preparing foamed and nonfoamed gels from aqueous solutions of polysaccharides having pendant carboxylate groups.

BACKGROUND OF THE ART

Gels formed by crosslinking polysaccharides bearing pendant carboxylate groups have been known and used for many years in the areas of dental health care and food preparation technologies. Of these gels, the most commonly encountered are composed of water-insoluble alginates which include, with the exception of magnesium, the alkaline earth metal salts and the group III metal salts of alginic acid. These water-insoluble alginate gels are typically formed by the chemical conversion of water-soluble alginates, in an aqueous solution, into water-insoluble alginates. This conversion usually is accomplished by the reaction of a water-soluble alginate with polyvalent cations released from a soluble di- or trivalent metal salt. The water-soluble alginates include the ammonium, magnesium, potassium, sodium, and other alkali metal salts of alginic acid.

The most common of the alginate gels is composed of calcium alginate. Sources for the crosslinking calcium ions used in the formation of these gels generally include calcium carbonate, calcium sulfate, calcium chloride, calcium phosphate, and calcium tartrate.

Controlling the time of gelation has traditionally been an integral part of conventional methods of preparing these calcium alginate gels and is usually accomplished by regulating the concentration of free calcium ions in the solution. Typically the concentration of free calcium ions is controlled by manipulation of the ionization rate of the calcium salt and/or by the inclusion of other compounds in the solution which react with the free calcium ions.

Conventional processes regulate the rate of ionization by selecting a calcium salt having the desired solubility and/or by adjusting the pH of the solution to increase the solubility of the calcium salt. The solubility of slightly soluble or water-insoluble calcium salts can be increased by lowering the pH of the solution. Generally the pH is lowered by the addition of an acid or by the addition of a substance such as an acid lactone that hydrolyzes to an acid. Commonly used pH adjusters include glucono-delta-lactone and acids such as acetic, adipic, citric, fumaric, lactic and tartaric acid.

The availability of calcium ions can also be controlled by the addition of gel retarders. Known gel retarders are salts having an anion that forms a water-insoluble or slightly water-soluble bond to the calcium ions. The retarder competes with the water-soluble alginate for the free calcium ions thereby depriving the alginate of some of the crosslinking ions and delaying gelation. Common retarders are the alkali metal phosphates, oxalates, and citrates.

Conventional methods for preparing these water-insoluble calcium alginate gels typically involve adding solid water-soluble alginate and solid calcium salt to an aqueous medium as disclosed in U.S. Pat. No. 3,455,701, and U.K. Patent Specification No. 1,579,324, published Nov. 19, 1980, or adding a solution or dispersion of calcium salt to an aqueous solution of water-soluble alginate as disclosed in U.S. Pat. No(s). 2,756,874, 4,381,947 and 4,401,456. Typically these methods include the addition of gel retarders and/or pH adjusters to provide control over the rate of gelation.

Traditionally, water-insoluble alginate gels have been used extensively in dental impression materials and as thickening or setting agents in food preparations. Recently, however, water-insoluble alginate gels have found utility as a form-in-place wound dressing material as disclosed in Swedish Patent Application Publication No. 424,956, published Aug. 23, 1982, and Applicant's copending U.S. patent application entitled "Alginate Hydrogel Foam Wound Dressing".

This newly discovered use for these gels brings with it new concerns with regard to the purity and sterility of the alginate gel being formed. For example, it is generally desirable that retarders and suspending agents which leave residual deposits in the alginate gel network not be present in the gel-forming components used to form alginate gel wound dressing materials. Furthermore, to be effective in preventing the contamination and infection of wounds it is generally desirable that the alginate gel wound dressing material be sterile prior to its application to the wound.

Theoretically, a sterile form-in-place alginate gel wound dressing may be prepared by either (1) sterilizing the gel-forming components separately prior to mixing and maintaining the components in a sterile environment before, during and after mixing until the composite material is applied to the wound, or (2) mixing the gel-forming components together first and then sterilizing the composite material immediately to application to the wound. The latter alternative, however, has little practical utility as it requires each batch of wound dressing material to be individually sterilized prior to its application to the wound, and thereby places unacceptable demands upon the time and facilities of the health care professional preparing the dressing. Likewise, in order for the former alternative to be useful, sterile gel-forming components, and a method of mixing these components while maintaining them in a sterile environment, must be available to the health care professional.

Additionally, it is desirable for the sterile gel-forming components to mix easily and quickly so as to minimize the demands on the health care professional's time and energy required to prepare the wound dressing material. Furthermore, it is desirable for the wound dressing material to gel quickly after application to the wound so as to minimize the inconvenience to the patient.

In light of these concerns, the present invention provides a self-contained gel-forming article useful for preparing sterile water-insoluble alginate gels, and a method for the quick and easy preparation of water-insoluble alginate gels without the use of suspending agents or gel retarders.

SUMMARY OF THE INVENTION

The present invention provides a novel method for preparing foamed and nonfoamed homogeneous gels from water-soluble polysaccharides bearing pendant carboxylate groups such as alginates. The method comprises mixing together two liquid components of a reactive two component system. One component, component A, is composed of a suspension of a water-insoluble di- or trivalent metal salt in an aqueous solution of water-soluble polysaccharide. The other component, component B, is composed of an aqueous solution of water-soluble acid. Optionally, component B may also contain additional amounts of the same or a different water-soluble polysaccharide as is dissolved in component A. When a foamed gel is desired, component A may also contain a substance which effervesces upon reaction with the water-soluble acid in component B.

Additionally, the present invention provides a self-contained gel-forming article ideally suited for the preparation of form-in-place water-insoluble polysaccharide gels by this novel method. The article comprises a first chamber containing a first component comprising a suspension of a water-insoluble di- or trivalent metal salt in an aqueous solution of water-soluble polysaccharide, a second chamber containing a second component comprising an aqueous solution of a water-soluble acid, and a means connected to said first and second chambers for intermixing said first and second components without exposing the components to the atmosphere or to any external mixing devices. Optionally, the first component may also contain a substance which effervesces upon reaction with an acid and/or the second component may also contain an additional amount of the same or a different water-soluble polysaccharide as is dissolved in the first component.

DETAILED DESCRIPTION OF THE INVENTION

The present invention produces a homogeneous polysaccharide gel by mixing together a first component (component A) comprising a suspension of water-insoluble di- or trivalent metal salt in an aqueous solution of water-soluble polysaccharide with a second component (component B) comprising an aqueous solution of a water-soluble acid. Optionally, component B may also have dissolved therein an additional amount of the same or a different water-soluble polysaccharide. Upon mixing, the acid reacts with the water-insoluble metal salt to form a water-soluble metal salt which is subsequently ionized. The cation released from the water soluble metal salt complexes with the pendant carboxylate groups of the polysaccharides causing the formation and precipitation of a gel. The rate of gel formation is governed by the rate of the reaction between the water-soluble acid and the water-insoluble metal salt and is thus controlled by the respective concentrations of metal salt and acid in the composite solution. Gel times ranging from less than one minute to several minutes have been observed and can be reproduced.

When a foamed gel is desired, a compound which effervesces upon reaction with the water-soluble acid in component B is added to the water-insoluble metal salt suspension of component A. Upon mixing, the water-insoluble metal salt reacts with the water-soluble acid to produce an ionizable metal salt which releases cations that gel the polysaccharide as described above. At the same time, the effervescent compound is reacting with the water-soluble acid and releasing gases which become entrapped by the forming gel causing the formation of a stable foamed gel.

The polysaccharides useful in the present invention are water-soluble, have pendant carboxylate groups, and complex with polyvalent cations to form gels. Suitable polysaccharides include the water-soluble salts of alginic, pectic and hyaluronic acids. The preferred polysaccharides are the ammonium, magnesium, potassium, sodium, and other alkali metal salts of alginic acid, and the most preferred polysaccharide is sodium alginate.

The water-insoluble di- or trivalent metal salts used in the present invention must satisfy two requirements. First, the water-insoluble metal salt must contain a di- or trivalent metal ion capable of complexing with the pendant carboxylate groups of the water-soluble polysaccharide to cause the formation of a water-insoluble polysaccharide gel. Second, the water-insoluble metal salt must react with a water-soluble acid to form a water-soluble metal salt. Preferred water-insoluble metal salts useful in the present invention include calcium carbonate, calcium phosphate dibasic ($CaHPO_4$), barium carbonate and zinc carbonate, with calcium carbonate being most preferred.

Water-soluble acids useful in the present invention may be chosen from monocarboxylic and dicarboxylic acids. Examples of suitable acids include acetic, adipic, fumaric, lactic and maleic acids. When the polysaccharide gel is to be used as a wound dressing material, the water-soluble acid selected should be biocompatible.

The effervescent compound must effervesce upon reaction with the water-soluble acid. Useful effervescent compounds may be chosen from the alkali metal carbonates with sodium carbonate being preferred.

Although recited as separate elements of Component A, it should be understood that in some cases the water-insoluble di- or trivalent metal salt and the effervescent compound may both be provided by a single compound. For example, the preferred water-insoluble metal salt (calcium carbonate) releases carbon dioxide gas upon reaction with the acid in Component B and, thus, produces a foamed gel without the inclusion of any other effervescent compounds. The resultant foamed gel, however, generally has a relatively high density and low void volume due to the small amount of carbon dioxide typically produced by this reaction. Thus, even if the water-insoluble di- or trivalent metal salt effervesces, it may still be desirable to include an additional effervescent compound in order to obtain a foamed gel having a greater void volume and lower density.

The article of the invention may take the form of a closed bag divided into two compartments by a removable closure, with one of the components contained within the compartment on one side of the closure and the other component contained within the compartment on the opposite side of the closure. In this embodiment of the article, mixing of the two components without exposing them to the atmosphere or to any external mixing devices can be accomplished simply by removing the closure and manually forcing the two components together.

Alternatively, the article may take the form of two permanently separated, component-containing chambers wherein each component-containing chamber is equipped with a discharge opening leading to a common mixing chamber. In this embodiment of the article, mixing of the two components without exposure to the atmosphere or external mixing devices can be accomplished by forcing each of the components from their respective chambers into the mixing chamber. Preferably the mixing chamber is in the form of a baffled discharge tube so that the components are mixed as they are discharged from the article through the discharge tube. A useful example of such an article is a double barrel syringe assembly equipped with a standard mixing tip.

As used herein, "double barrel syringe assembly" refers to a syringe having two separate barrels arranged side by side. Each barrel is equipped with a separate plunger to force the material contained therein out through a discharge opening. One end of each plunger is inside its respective barrel and forms a seal with the walls of the barrel. The other end of each plunger is outside of its respective barrel so that force from an external source can be applied to the plunger. The two plungers can be connected together at their ends outside of the barrels so that force exerted on the plungers will generate the same pressure within each barrel, and will displace both plungers an equal distance.

The gel-forming method and article of the invention are ideally suited for the preparation of sterile, form-in-place, water-insoluble alginate gel wound dressing materials. The components mix easily and quickly, requiring little effort on the part of the preparer. Furthermore, the gel-forming reaction can be made to occur within a few minutes with the rate of gelation being controlled, without the use of gel retarders, simply by regulating the concentrations of the water-insoluble metal salt and the water-soluble acid in the gel-forming composition.

Additionally, since the water-insoluble di- or trivalent metal salt is suspended in an aqueous solution of water-soluble alginate, there is no need for any extraneous suspending agents. The metal salt suspension can be made sufficiently stable to provide the gel-forming article with a shelf-life of sufficient duration to make commercial distribution of the article feasible, simply by correctly matching the size of the metal salt particles and the viscosity of the alginate solution. The viscosity of the alginate solution is dependent upon the molecular weight of the water-soluble alginate chosen and the concentration of the alginate in the solution. The viscosity of the alginate solution increases as the molecular weight of the alginate increases and as the concentration of alginate in the solution increases. In addition, the viscosity of the water-soluble alginate solution can be increased by partially gelling the alginate via the addition of a small amount of a water-soluble acid and/or a small amount of a water-soluble di- or trivalent metal salt to the solution.

Furthermore, the gel-forming article is a self-contained unit having all of the reactive gel-forming materials enclosed therein and is equipped with a mixing means capable of mixing the gel-forming components together without exposing them to the atmosphere or to any external mixing devices. Thus the user of the article can form an alginate gel without adding any additional material to the enclosed ingredients, without exposing the enclosed ingredients to the atmosphere, the hands of the user or any mixing implements. Accordingly, there is no opportunity for adding too much or too little material, no requirement of a mixing vessel or mixing instrument, and no opportunity for contamination of the material during mixing. Therefore, if the chambers of the article are sterile prior to being filled with sterile gel-forming components, the article can produce sterile water-insoluble alginate gels useful as wound dressing materials.

The invention is further illustrated by the following non-limiting examples wherein all percentages are by weight unless otherwise specified.

EXAMPLE I

Preparation of a Slightly Foamed Alginate Gel

A suspension of calcium carbonate ($CaCO_3$) in an aqueous solution of sodium alginate was prepared by adding 0.21 g solid $CaCO_3$ to 38.6 g of a 4.5% aqueous sodium alginate solution.

An aqueous sodium alginate solution containing enough acetic acid to react with all of the $CaCO_3$ was prepared by adding 0.35 g of a 50% aqueous acetic acid solution to 37.66 g of a 4.5% aqueous sodium alginate solution.

The two alginate solutions were loaded into a double-barrel syringe assembly fitted with a 12-element mixing tip. The two solutions mixed as they were discharged through the tip and formed a slightly foamed homogeneous gel in approximately one minute.

EXAMPLE II

Preparation of a Highly Foamed Alginate Gel

A suspension of calcium carbonate ($CaCO_3$) and sodium carbonate ($Na_2CO_3$) in an aqueous sodium alginate solution was prepared by adding 0.41 g $CaCO_3$ and 0.83 g $Na_2CO_3$ to 36.64 g of a 4.5% aqueous sodium alginate solution.

An aqueous sodium alginate solution containing acetic acid was prepared by adding 1.4 g of a 50% aqueous acetic acid solution to 37.0 g of a 4.5% aqueous sodium alginate solution.

The two alginate solutions were mixed via the double-barrel syringe assembly of Example I. Foaming began immediately upon mixing and a stable highly foamed homogeneous gel formed in approximately two minutes.

What is claimed is:

1. A method of making a polysaccharide gel from water-soluble polysaccharides bearing pendant carboxylate groups comprising mixing together a first liquid component comprising an aqueous solution of one of said water-soluble polysaccharides having suspended therein particles of a water-insoluble di- or trivalent metal salt that will react with an acid to form a water-soluble metal salt, and that has a di- or trivalent metal ion capable of complexing with the pendant carboxylate groups of said water-soluble polysaccharides to form a water-insoluble polysaccharide gel; and a second liquid component comprising an aqueous solution of a water-soluble acid.

2. The method of claim 1 wherein said water-soluble polysaccharide is selected from the group consisting of the ammonium, magnesium, potassium, sodium, lithium, rubidium, and cesium salts of alginic acid.

3. The method of claim 1 wherein said water-insoluble di- or trivalent metal salt is selected from the group consisting of calcium carbonate, calcium phosphate dibasic, barium carbonate and zinc carbonate.

4. The method of claim 1 wherein said water-soluble acid is selected from the group consisting of acetic, adipic, fumaric and lactic acids.

5. The method of claim 1 wherein said second component further comprises water-soluble polysaccharide bearing pendant carboxylate groups dissolved therein.

6. The method of claim 5 wherein the water-soluble polysaccharide in both said first and second components is of the same composition.

7. A method of making an alginate gel from water-soluble alginates comprising mixing together a first liquid component comprising a suspension of calcium carbonate particles in an aqueous solution of sodium alginate, and a second liquid component comprising an aqueous solution of sodium alginate and acetic acid.

8. A method of making a foamed polysaccharide gel from water-soluble polysaccharides bearing pendant carboxylate groups comprising mixing together a first liquid component comprising (a) an aqueous solution of one of said water-soluble polysaccharides, (b) particles of a water-insoluble di- or trivalent metal salt that will react with an acid to form a water-soluble metal salt, and that has a di- or trivalent metal ion capable of complexing with the pendant carboxylate groups of said water-soluble polysaccharides to form a water-insoluble polysaccharide gel, suspended therein, and (c) an effervescent compound that effervesces upon reaction with an acid; and a second liquid component comprising an aqueous solution of a water-soluble acid.

9. The method of claim 8 wherein said water-soluble polysaccharide is selected from the group consisting of the ammonium, magnesium, potassium, sodium, lithium, rubidium and cesium salts of alginic acid.

10. The method of claim 8 wherein said water-insoluble di- or trivalent metal salt is selected from the group consisting of calcium carbonate, calcium phosphate dibasic, barium carbonate and zinc carbonate.

11. The method of claim 8 wherein said water-soluble acid is selected from the group consisting of acetic, adipic, fumaric and lactic acids.

12. The method of claim 8 wherein said second component further comprises water-soluble polysaccharide bearing pendant carboxylate groups dissolved therein.

13. The method of claim 12 wherein the water-soluble polysaccharide in both said first and second components is of the same composition.

14. The method of claim 8 wherein said effervescent compound is selected from the group consisting of the alkali metal carbonates.

15. A method of making a foamed alginate gel from water-soluble alginates comprising mixing together a first liquid component comprising (a) an aqueous solution of sodium alginate, (b) particles of calcium carbonate suspended therein, and (c) sodium carbonate; and a second liquid component comprising an aqueous solution of sodium alginate and acetic acid.

16. A self-contained gel-forming article comprising:
 (1) a first chamber containing a first component comprising an aqueous solution of a water-soluble polysaccharide bearing pendant carboxylate groups having suspended therein particles of a water-insoluble di- or trivalent metal salt that will react with an acid to form a water-soluble metal salt, and that has a di- or trivalent metal ion capable of complexing with the pendant carboxylate groups of said water-soluble polysaccharide to form a water-insoluble polysaccharide gel;
 (2) a second chamber containing a second component comprising an aqueous solution of a water-soluble acid; and
 (3) a means connected to said first and second chambers for intermixing said first and second components without exposing said components to the atmosphere or to any external mixing devices.

17. A self-contained gel-forming article as recited in claim 16 wherein said water-soluble polysaccharide is selected from the group consisting of the ammonium, magnesium, potassium, sodium, lithium, rubidium and cesium salts of alginic acid.

18. A self-contained gel-forming article as recited in claim 16 wherein said water-insoluble di- or trivalent metal salt is selected from the group consisting of calcium carbonate, calcium phosphate dibasic, barium carbonate and zinc carbonate.

19. A self-contained gel-forming article as recited in claim 16 wherein said water-soluble acid is selected from the group consisting of acetic, adipic, fumaric and lactic acids.

20. A self-contained gel-forming article as recited in claim 16 wherein said second component further comprises water-soluble polysaccharide bearing pendant carboxylate groups dissolved therein.

21. A self-contained gel-forming article as recited in claim 20 wherein the water-soluble polysaccharide in both said first and second components is of the same composition.

22. A self-contained gel-forming article as recited in claim 16 wherein said article is formed of a closed bag divided into said first and second chambers by a removable closure.

23. A self-contained gel-forming article as recited in claim 16 wherein said first and second chambers are permanently separated and each of said first and second chambers have a discharge opening leading to a common mixing chamber.

24. A self-contained gel-forming article as recited in claim 23 wherein said mixing chamber comprises a baffled discharge tube.

25. A self-contained gel-forming article as recited in claim 24 comprising a double barrel syringe assembly equipped with a mixing tip.

26. A self-contained gel-forming article comprising: (a) a double barrel syringe assembly equipped with a mixing tip, (b) a suspension of calcium carbonate particles in an aqueous solution of sodium alginate contained within one of said barrels, and (c) an aqueous solution of sodium alginate and acetic acid contained within said other barrel.

* * * * *